United States Patent [19]
Ferris

[11] Patent Number: 6,003,177
[45] Date of Patent: Dec. 21, 1999

[54] PILLOW

[76] Inventor: Robyn Wendy Ferris, Victoria, Australia

[21] Appl. No.: 09/155,453
[22] PCT Filed: Apr. 8, 1997
[86] PCT No.: PCT/AU97/00222
  § 371 Date: Sep. 29, 1998
  § 102(e) Date: Sep. 29, 1998
[87] PCT Pub. No.: WO97/38611
  PCT Pub. Date: Oct. 23, 1997

[30] Foreign Application Priority Data

Apr. 15, 1996 [AU] Australia .................. PN9260

[51] Int. Cl.⁶ ....................................... A47G 9/00
[52] U.S. Cl. ........................ 5/636; 5/645; 5/643
[58] Field of Search ............... 5/636, 638, 639, 5/640, 643, 645, 953

[56] References Cited

U.S. PATENT DOCUMENTS

| | | |
|---|---|---|
| 1,386,652 | 8/1921 | Patton . |
| 2,167,622 | 8/1939 | Bentivoglio . |
| 2,728,926 | 1/1956 | Emery ............ 5/338 |
| 3,239,854 | 3/1966 | Freedlander ....... 5/337 |
| 3,757,365 | 9/1973 | Kretchmer ......... 5/338 |
| 4,118,813 | 10/1978 | Armstrong ........ 5/337 |
| 4,197,604 | 4/1980 | Nakamura ......... 5/437 |
| 4,207,636 | 6/1980 | Ceriani ........ 5/636 X |
| 4,287,621 | 9/1981 | Kertz ............. 5/636 |
| 4,320,543 | 3/1982 | Dixon ............. 5/434 |
| 4,375,112 | 3/1983 | Leonhart .......... 5/436 |
| 4,536,905 | 8/1985 | DeSantis .......... 5/434 |
| 4,726,087 | 2/1988 | Schaefer et al. ... 5/434 |
| 4,731,891 | 3/1988 | Scheurer et al. ... 5/434 |
| 4,752,064 | 6/1988 | Voss ............ 269/328 |
| 4,759,089 | 7/1988 | Fox ............... 5/434 |
| 4,777,855 | 10/1988 | Cohen ......... 5/636 X |
| 4,780,920 | 11/1988 | White ............. 5/436 |
| 4,788,728 | 12/1988 | Lake .............. 5/434 |
| 4,850,067 | 7/1989 | Latorre ........... 5/431 |
| 4,899,405 | 2/1990 | Rothbard .......... 5/636 |
| 4,908,893 | 3/1990 | Smit .............. 5/434 |
| 4,908,894 | 3/1990 | Sanders ........... 5/436 |
| 4,916,765 | 4/1990 | Castronovo, Jr. . 5/643 X |
| 4,918,774 | 4/1990 | Popitz ......... 5/636 X |
| 4,924,540 | 5/1990 | Main .............. 5/436 |
| 4,996,734 | 3/1991 | Rowe .............. 5/434 |
| 5,014,377 | 5/1991 | Dixon ............. 5/636 |
| 5,027,457 | 7/1991 | Sweet ............. 5/437 |
| 5,054,143 | 10/1991 | Javaher ........... 5/434 |
| 5,084,926 | 2/1992 | Wattie et al. ..... 5/636 |
| 5,123,132 | 6/1992 | Dixon ............. 5/636 |
| 5,123,133 | 6/1992 | Albert ............ 5/639 |
| 5,127,117 | 7/1992 | Bridges ........... 5/636 |
| 5,138,732 | 8/1992 | Wattie et al. ..... 5/636 |
| 5,163,194 | 11/1992 | Dixon ............. 5/636 |
| 5,237,714 | 8/1993 | Baron ............. 5/636 |
| 5,367,731 | 11/1994 | O'Sullivan ........ 5/645 |
| 5,533,218 | 7/1996 | Fahy .......... 5/643 X |
| 5,557,816 | 9/1996 | Pedersen et al. ... 5/645 |
| 5,682,633 | 11/1997 | Davis ......... 5/645 X |

FOREIGN PATENT DOCUMENTS

| | | |
|---|---|---|
| 73909 | 1/1978 | Australia . |
| 73961 | 2/1978 | Australia . |
| 34783/78 | 4/1978 | Australia . |
| 43078/85 | 12/1985 | Australia ........ A47G 9/00 |
| 108374 | 7/1990 | Australia ............. 6/9 |
| 0 384 583 A1 | 8/1990 | European Pat. Off. ... A61G 7/057 |
| 2 198 341 | 6/1988 | United Kingdom ..... A47G 9/00 |
| WO 95/28861 | 11/1995 | WIPO ........... A47G 9/00 |

Primary Examiner—Terry Lee Melius
Assistant Examiner—Robert G. Santos
Attorney, Agent, or Firm—Caesar, Rivise, Bernstein, Cohen & Pokotilow, Ltd.

[57] ABSTRACT

A pillow is disclosed which comprises a central portion having a pair of head support limbs which curve outwardly from the head end of the pillow towards a foot end of the pillow. A pair of neck, chin and jaw support limbs extend outwardly at the foot end and inwardly of the head support limbs. The limbs are provided with curved, concave surfaces and define air breathing spaces between the limbs.

10 Claims, 8 Drawing Sheets

PILLOW

This invention relates to a pillow and in particular to a pillow to counteract obstructive sleep apnoea (USA), snoring and other breathing or posture problems during sleep.

Some pillows used for correcting head position while sleeping encourage people to sleep in supine position but sleeping lying upon the back creates breathing problems and can be dangerous for people suffering from OSA wherein the tongue and soft tissue fall back blocking airways or, in the case of snoring, the airway narrows. OSA sufferers need to sleep in side/coma or front positions to avoid or minimise these problems. Many conditions result in restless and disturbed sleep due to incorrect positioning of the head upon a pillow because many pillows do not allow for the natural movements of the head of a sleeping person. When in a side or coma sleeping position a sleeping person's face can turn into a pillow and become embedded, which causes pressure around the nose, upper cheek and eye areas. This pressure causes nasal obstruction and discomfort owing to the facial pressure and heat build up on cheeks in turn producing scrunch marks to these areas creating a cosmetic problem. Some people attempt to compensate for insufficient breathing space and discomfort by placing hands together under the head forming space between upper and lower arm. Pounding a temporary hollow in the pillow with one's fist is not a proper solution. Many people, particularly the elderly, have problems with stiffness and lack of flexibility of the cervical neck region of the spine. During sleep most therapeutic pillows result in a person's neck being held in an unnatural position to receive support and do not allow for natural movement of a person's head upon a pillow.

In further detail, problems which are associated with various kinds of conventional pillows are discussed below.

Soft-filled pillows are generally pillows filled with a soft material. If a user wishes to adopt the side/coma position the pillow is arranged so that the neck is supported, however, the face is inevitably embedded in the pillow. This causes obstruction of the nasal passage and mouth making it difficult to breathe. The uncomfortable pressure being exerted to the facial area around the upper cheek, eye and often ears produces a build up of heat on the face, especially in hot weather causing a feeling of restlessness. When asleep the neck relaxes and bends the chin towards the chest. When this happens this type of pillow does not provide good support for the chin and allows it to twist downwards. The strategy often used to alleviate one or more of these problems is for the user to bend the elbow and bring the hand up to rest the head, thereby elevating the head off the pillow. The space formed by the upper and lower arm creates a breathing space that enables the person to breathe without obstruction and reduces the pressure on the face. However, the arm eventually becomes tired and the blood flow often is restricted because of the bent elbow. Another way is for the user to put the face over the edge of the pillow if they wish to side or front sleep in an unobstructed breathing environment but they still experience the feeling of pressure. Both of these methods often result in very restless sleep and inevitably the body takes the line of least resistance and turns on the back. Though this may be comfortable for some, it is undesirable for snorers and possibly dangerous for obstructive sleep apnoea sufferers.

The main problem with molded foam pillows of conventional design is due to the inflexibility to adapt to individual differences. These pillows are usually designed with a hump for the neck support and a hollow or valley in the centre for the head section. This style may be suitable for some for back sleep but usually the neck is overstretched in this position which allows the jaw to open and in turn the tongue and soft tissue to fall backward, which results in snoring or the obstruction of the airway. If a user wishes to side sleep the neck must be held in a certain position to gain any benefit from such a pillow. While the weight of the head is consciously held in the designated position often the neck is overstretched. However, when the neck and body relax as automatically happens while asleep the head will take on a more natural position bending a few degrees towards the chin. Even if this occurs to the slightest degree, the neck and head become misaligned with the intended designated position for them. Because the head is now positioned on top of the neck support/hump section the neck does not have any support. This causes neck and shoulder pain and puts a lot of strain on the spine.

Some prior art pillows have designed a hollow or hole for a pressure free and unobstructed breathing space. These hollows or holes are embedded in the central part of the pillow and are not adjustable for individual size heads. Because these holes are in the central part of the pillow the back of the head does not receive the correct support, but most importantly, because they are embedded in the pillow if the face is turned downwards even slightly the exhaled air is trapped in the hollow and then reinhaled. This is not at all desirable as carbon dioxide can build up in the blood making the user feel tired on waking.

The object of the present invention is to provide a pillow which overcomes the above disadvantages.

The present invention provides a pillow including;

a pillow body which has;

(a) a central portion having a first bed head end and a second foot end;

(b) a pair of head support limbs extending outwardly from the central portion and curving from the bed head end towards the foot end;

(c) a pair of neck, chin and jaw support limbs extending outwardly from the central portion at the foot end of the central portion and being spaced inwardly of the head support limbs;

(d) a breathing space being defined between each adjacent head support limb and neck, jaw and chin support limb, the breathing space extending from an intermediate position of the central portion between the bed head end and the foot end of the central portion and curving outwardly and towards the foot end of the central portion; and (e) the head support limbs and neck, jaw and chin support limbs having surfaces which are curved downwardly from an upper position on the upper surface of the limbs towards a bottom position adjacent the bottom surface of the limbs so that the breathing spaces taper from a relatively wide opening between the upper positions of the limbs to a relatively narrower opening at the bottom positions of the limbs.

The pillow according to this invention provides excellent neck jaw and chin and head support for a user in any position on the pillow. In particular, it provides support for natural movement of the neck and head during sleep. The curved and tapering breathing slot provides an unobstructed breathing opening or environment for the user in any position the user takes up when resting in an awake condition or when the neck moves in a natural fashion during the course of sleep. Furthermore, the curved surfaces of the head and neck, jaw and chin support limbs provides a pressure free environment for the facial area in any position during sleep and eliminates heat and discomfort around the upper cheek and eye areas. The reduced pressure also provides a cosmetic benefit by reducing or eliminating pressure marks around delicate areas. The pillow also provides flexibility for ease of adjustment during the night should that be necessary by simply moving the limbs as is required should slight adjustments be required or desired for personal preference.

Preferably the pillow body includes a separate base section which can be removed to alter the height of the pillow.

Preferably the pillow has a cover conforming in shape to the pillow body.

In one embodiment the cover may include an inner liner to form a pouch for receipt of soft filling material so that soft filling material can be included in the pouch to change the height and/or shape of the pillow, the inner liner extending along at least part of the length of the neck, jaw and chin limbs and the central portion adjacent the foot end of the pillow. An inner liner may also be provided at the head support limbs.

Preferably cuts are provided in the central portion extending inwardly from the breathing space for accommodating movement of the limbs with respect to one another and the central portion.

The bed head end of the pillow may also be provided with a V-shaped profile to also assist in movement of the head support limbs and to prevent buckling with respect to the central portion.

Preferably the breathing spaces are in the form of open spaces extending completely through the pillow.

Preferably additional soft filling may be provided for location between the pillow body and the outer cover for changing the height and/or contour of the central portion or limbs.

Preferably the pillow body and the outer cover are provided in a pillow slip.

Preferably the upper surface of the pillow body is convoluted or egg carton shaped.

Preferred embodiments of the invention will be described, by way of example, with reference to the accompanying drawings in which.

Figure 1:
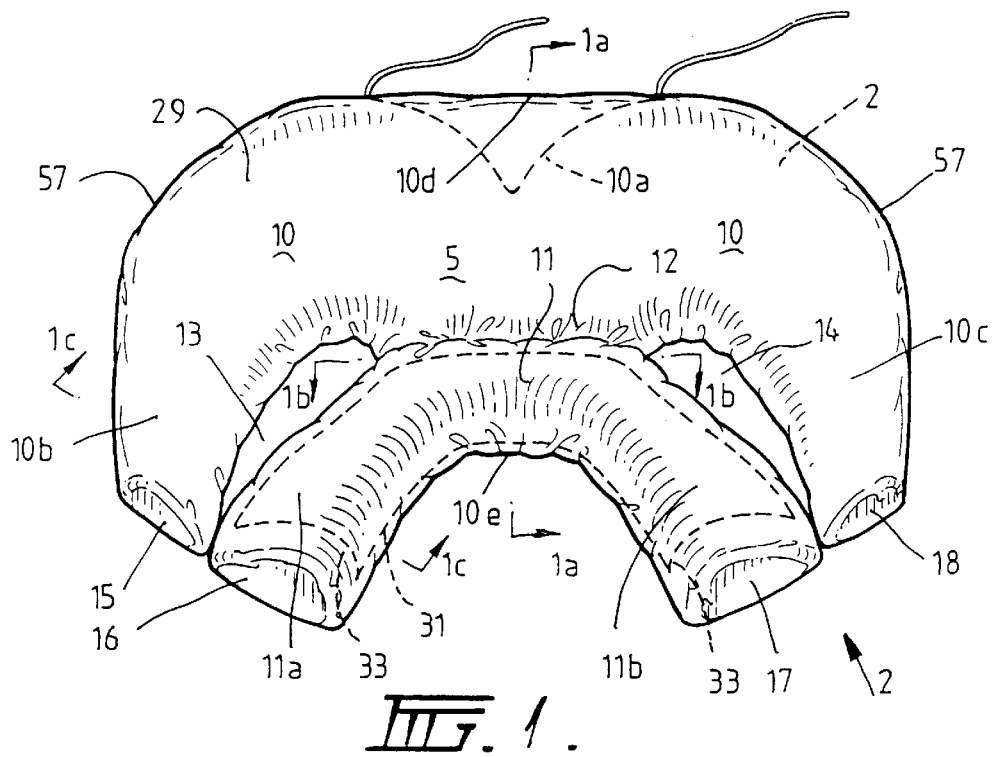
FIG. 1 is a view of a pillow embodying the invention shown in an outer cover.

With reference to FIG. 1 a pillow embodying the invention is shown generally in plan view. The pillow comprises a pillow body 2 (shown in an exploded configuration in FIG. 4) which is located inside an outer cover 29 as shown in FIG. 1. The pillow body 2 has the same shape as the outer cover 29 except that the pillow body 2 has a generally V-shaped profile 10a at bed head end 10d of the pillow whereas the cover 29 is generally straight at the bed head end 10d of the pillow. The pillow also has a foot end 10e and a central portion 5 is defined between the bed head end 10d and foot end 10e of the pillow.

A pair of head support limbs 10b and 10c extend in curved fashion from the bed head end 10d of the pillow outwardly and downwardly towards the foot end 10e of the pillow.

A pair of neck, jaw and chin support limbs 11a and 11b extend outwardly and downwardly from the central portion 5 and inwardly of the limbs 10b and 10c.

Air breathing spaces in the form of gaps or slots 13 and 14 are defined between the limbs 10b and 11a and between the limbs 10c and 11b respectively. As is clearly shown in FIG. 1 the air breathing slots or gaps 13 and 14 commence at an intermediate position of the central portion 5 and extend outwardly in curved fashion towards foot end 10e. Thus the slots 13 and 14 are arcuate and have a radius of curvature which is the same as that followed by the mouth and nasal region of a user when a user's head moves during sleep as a person's chin moves towards the user's chest. This relationship is more clearly shown in FIGS. 10 to 17 which will be described hereinafter. As is clearly shown in FIGS. 1 and 2 the limbs 10b, 10c, 11a and 11b terminate in truncated ends 15, 16, 17 and 18 respectively. The limbs 11a and 11b may be slightly higher adjacent ends 16 and 17 than the remainder of the limbs 11a and 11b and portion 11.

The central portion 5 has a region 11 generally between the limbs 11a and 11b which forms the primary neck support section of the pillow. The portions of the pillow labelled 10 which extend across the central portion 5 and form transitions into the limbs 10b and 10c generally form the primary head support regions of the pillow.

Shoulders 57 of the limbs 10b and 10c are rounded so if the limbs 10b and 10c are moved towards a bed head (not shown) to provide more freedom of movement and prevents blocking of movement of the limbs by the bed head.

Figure 1A:
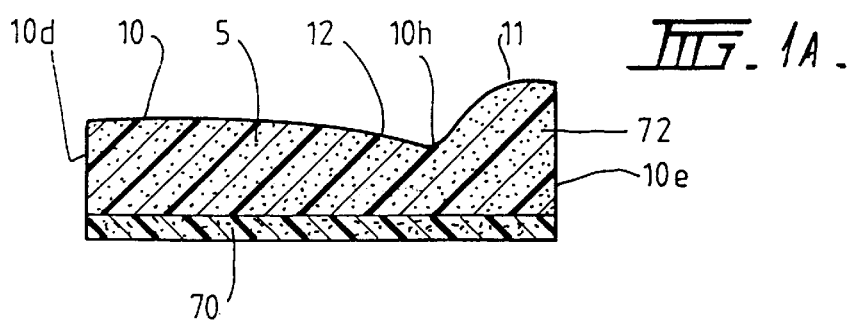
FIG. 1A is a cross-sectional view of the pillow body with the outer cover removed along the line 1a—1a of FIG. 1.

As is best shown in FIG. 1A the central portion 5 in the longitudinal direction from the bed head end 10d to the foot end 10e is generally flat from end 10d to a bridging portion 12 between the primary head support region 10 and the primary neck support region 11 and then rises upwardly to the primary neck support region 11 so that the primary neck support region 11 is somewhat higher than the primary head support region 10. A small dip or recess 10h may be provided at the commencement of the portion 11 to provide room for a persons ear to reduce pressure against the ear. As is also shown in FIGS. 2 and 3 and the cross-sectional view forming FIG. 1B the central portion 5 in the vicinity of the bridge 12 is curved in convex fashion as shown by surface 12a in FIG. 1B.

Figure 1B:
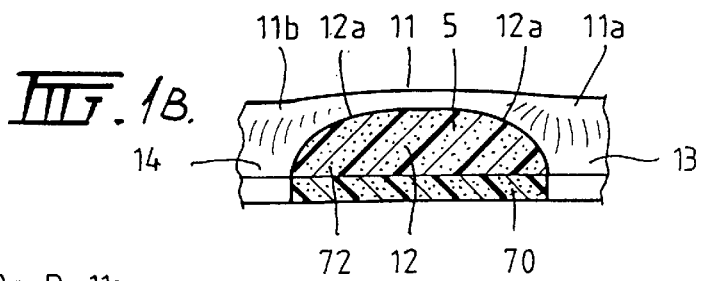
FIG. 1B is a cross-sectional view along the line 1b—1b of FIG. 1 also with the outer cover removed.
Figure 1C:
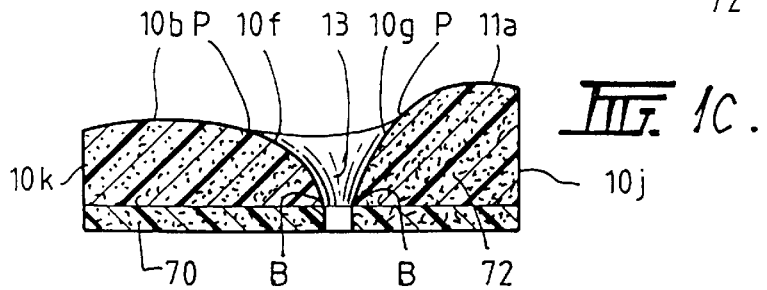
FIG. 1C is a view along the line 1c—1c of FIG. 1 also with the outer cover removed.
Figure 2:
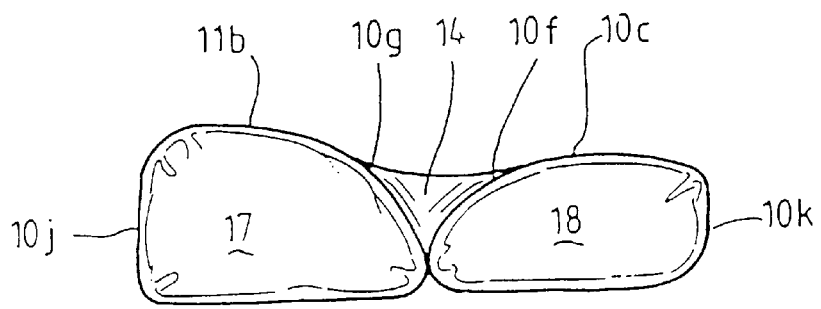
FIG. 2 is a view from the direction of pointer 2 in FIG. 1.
Figure 3:
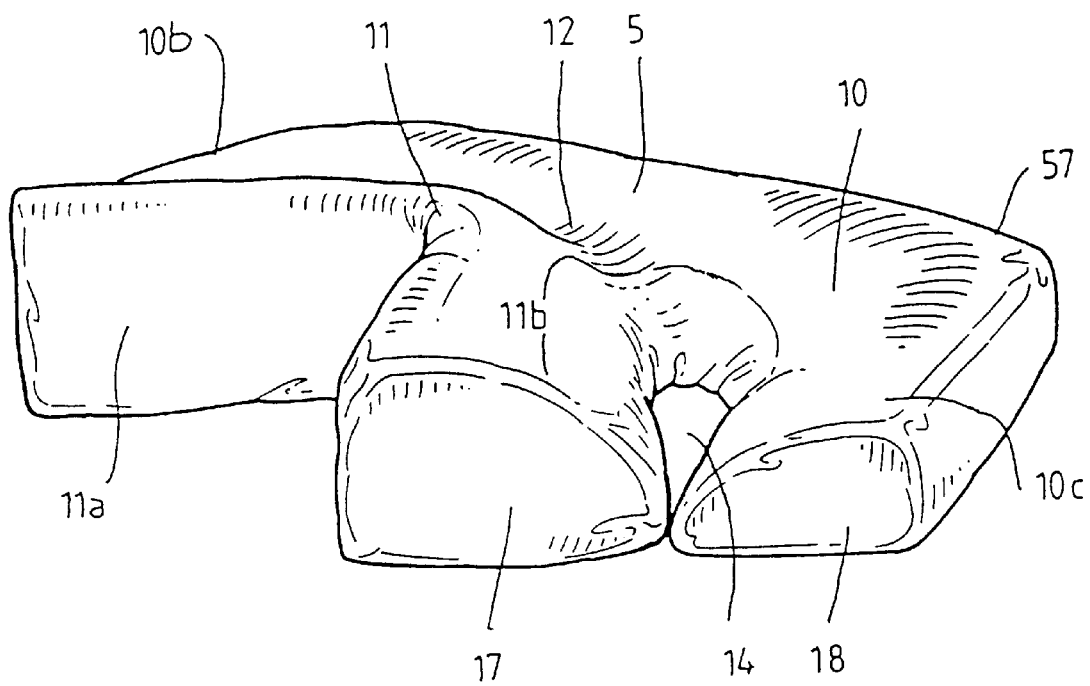
FIG. 3 is an upper side perspective view of the pillow of FIG. 1.

As is also evident from FIGS. 2, 3 and the cross-sectional views forming FIGS. 1B and 1C the neck support region 11 and the neck, jaw and chin support limbs 11a and 11b are higher than the primary head support regions 10 and head support limbs 10b and 10c.

As is also best shown in FIGS. 2 and 1C the limbs 10b and 11a have inner surfaces 10f and 10g which are curved downwardly in convex fashion from an upper position shown by points P to a lower position shown by points B so that the slot 13 defined between the limbs 10b and 11a (and also between the limbs 10c and 11b) tapers downwardly from a generally large upper opening immediately between the points P to a relatively narrower opening between the points B. Outer surfaces 10h and 10j of the limbs 10b and 11a (and also of the limbs 10c and 11b) may be generally vertical surfaces as shown in FIG. 1C or, if desired, may be curved or rounded in convex fashion as shown in FIG. 2 or may be concave.

Figure 4:
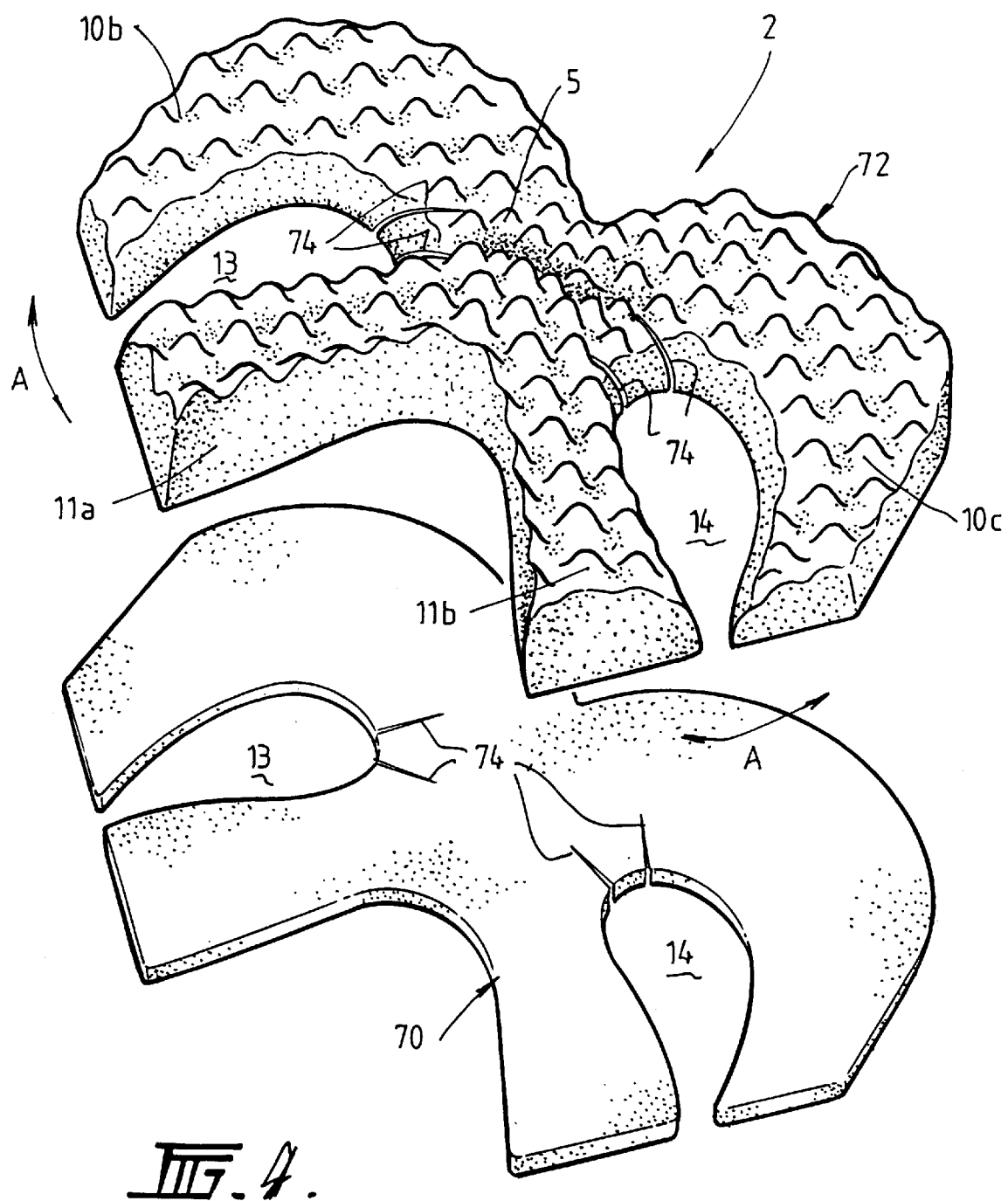
FIG. 4 is an exploded perspective view of the pillow body.

As best shown in FIG. 4 the pillow body 2 is formed of a base layer 70 which is separate from an upper layer 72. Though FIGS. 1A to 1C generally show the pillow body 2 with a smooth outer surface, the outer surface of the upper layer 72 may be convoluted or egg carton shaped as is shown in FIG. 2 to assist in pressure distribution over the areas of the user's head which are contacted by the pillow. FIGS. 1A to 1C, 5 and 6 show the upper surfaces of the upper body 72 smooth or planar rather than convoluted to more clearly and easily show the curvature of the surfaces. The upper layer 72 is contoured in the manner described with reference to FIGS. 1A to 1C. As can clearly be seen in FIG. 1C the base layer 70 merely provides a generally thin height adjusting layer which can be removed or used as is desired to adjust the height of the pillow. Thus, if a relatively low pillow is desired as may be the case if a person prefers to sleep on their front or back the base layer 70 can be removed. If a relatively higher pillow is required for back, side or coma position sleep, then the base layer 70 is used to slightly increase the height or thickness of the pillow to suit shoulder height when sleeping in those positions.

The basic contouring of the pillow which provides the curved surfaces as described with reference to FIGS. 1A to 1C is all provided on the upper layer 72 so, notwithstanding removal of the base layer 70 the pillow will still have the shape, characteristics and contouring which has been described with reference to FIGS. 1A, 1B and 1C.

As is best shown in FIG. 4 the base layer 70 and upper body 72 may be provided with cuts 74 which extend inwardly into central portion 5 from the inner ends of slots 13 and 14 to facilitate movement of the limbs 10b, 11a, 10c and 11b generally in the direction of double-headed arrows A in FIG. 4 to adjust the position of the limbs with respect to one another and also with respect to the central portion 5 to suit a user's personal needs.

Figure 7:
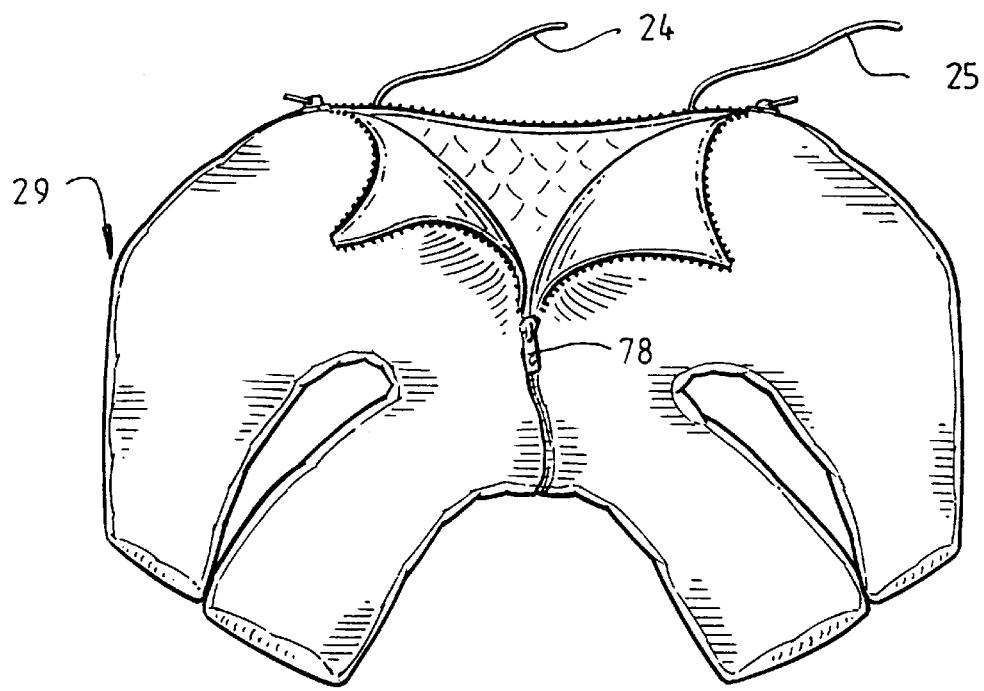
FIG. 7 is a plan view showing the outer cover on the pillow body.
Figure 8:
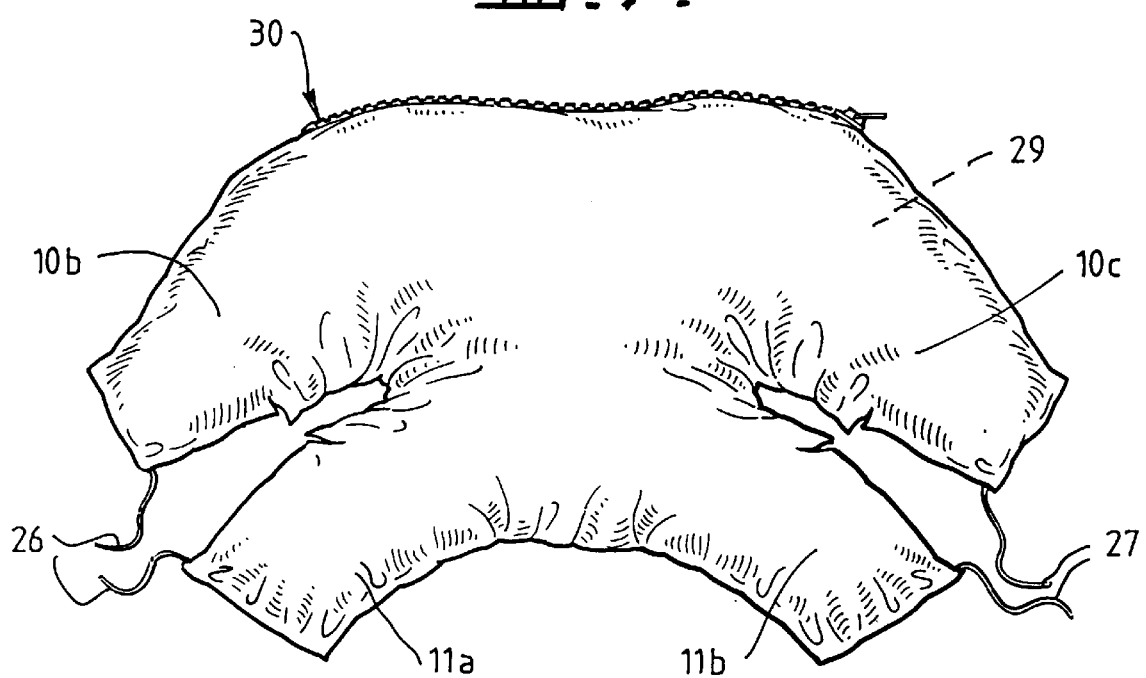
FIG. 8 is a further view showing the pillow in a pillow case.

For example, FIG. 7 shows a position of the limbs in a generally closed position where the truncated ends 15, 16 and 17, 18 generally touch one another to close the slots 13 and 14 or maybe move to an open position as shown in FIG. 8 where the truncated ends 15, 16 and 17, 18 are spaced well apart from one another. It should be noted that even in the closed position shown in FIG. 7 the air breathing gaps or slots 13 and 14 are closed only at the truncated ends and not completely shut off so that the air breathing slots and gaps are always provided notwithstanding closure of the limbs 10b, 11a or 10c, 11b.

Figure 5:
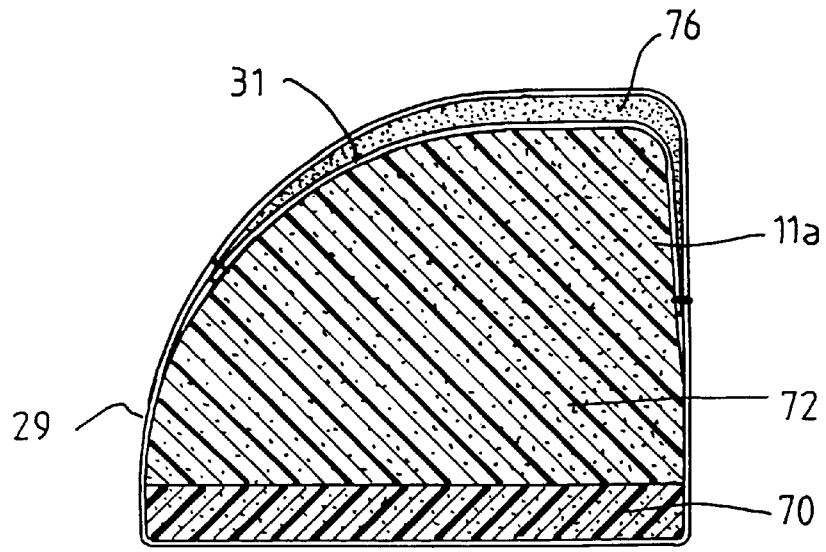
FIG. 5 is a cross-sectional view through the neck support limb according to one embodiment of the invention.
Figure 6:
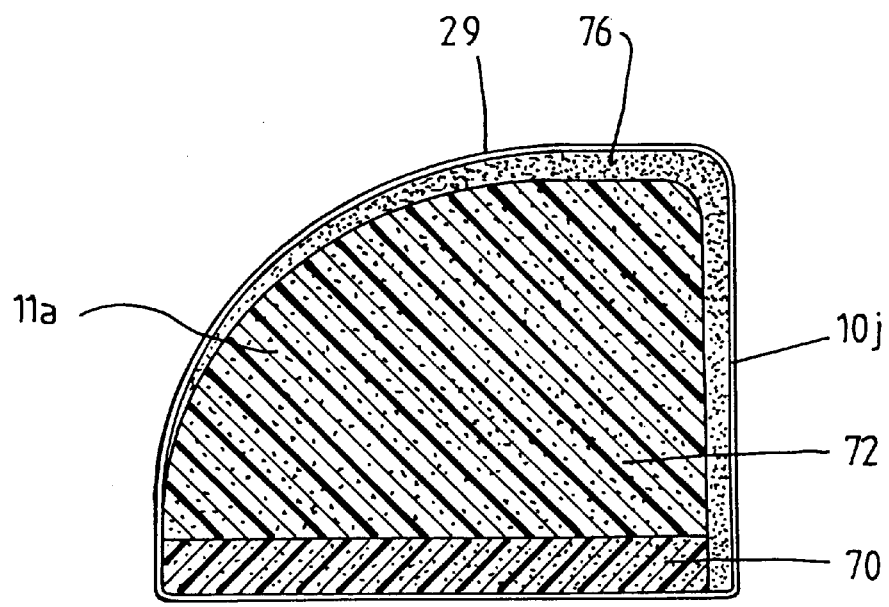
FIG. 6 is a cross-sectional view similar to FIG. 5 according to a second embodiment.

FIGS. 5 and 6 show cross-sectional views through limb 11a showing various embodiments of the invention by which additional soft filling 76 can be added to increase the height of the limbs or slightly change their contour. In the embodiment in FIG. 5 outer cover 29 is shown and an inner liner 31 is sewn to the inner surface of the cover 29. As is shown in dotted lines in FIG. 1 the inner liner 31 extends across primary neck support region 11 and along the majority of the length of the limbs 11a and 11b. The liner 31 is left open from the cover 29 at ends 33 (see FIG. 1) and soft material stuffing can be stuffed in between the liner 31 and cover 29 to form the filling 76 shown in FIG. 5 to slightly increase the height of the primary neck support region 11 and also part of the limbs 11a and 11b if desired. Alternatively the ends 33 could be stitched closed on the pouch filled from a central open location. The filling 76 may also provide a softer feel to the pillow.

FIG. 6 shows a further embodiment in which additional soft filling material 76 is located between the upper body 72 and the outer cover 29 not only in the vicinity of the top of the limb 11a but also down the outer surface 10j if the neck support needs to be wider as well as higher. The additional stuffing can be used together with the inner liner 31 shown in FIG. 5. FIG. 6 merely shows the embodiment in which the inner liner 31 is completely omitted. However, the inner liner 31 does provide the advantage of localising and ensuring correct location of the soft filling material 76 to provide increase in height of the pillow if desired.

FIG. 7 shows the outer cover 29 from beneath in which a zipper 78 or other suitable attachment such as velcro fasteners are used to close the outer cover 29 over the pillow body 2. The outer cover 29 is preferably formed of a soft, slightly padded material such as quilt material or the like. In this embodiment ties 24 and 25 may be provided on the cover 29 for pulling the portions of the cover 29 adjacent the V-shaped profile 10a of the body 2 together to in turn slightly close the V-shaped profile which will assist in moving the limbs 10b and 10c outwardly from the position shown in FIGS. 1 and 7 and then tying them in that position.

FIG. 8 is a view showing an outer pillow slip 30 over the cover 29. The outer pillow slip 30 is intended to be removed periodically for washing. The outer pillow slip 30 may be provided with ties 26 and 27 which can be used to tie the limbs 10b, 11a and 10c, 11b together in the closed position if desired.

Figure 9:
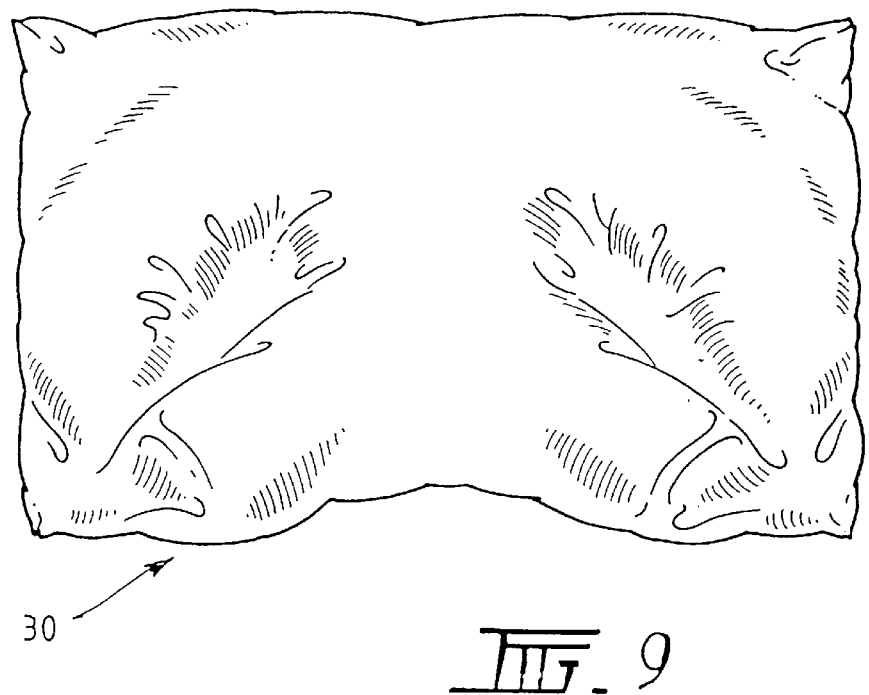
FIG. 9 is a view of the pillow inside a standard pillow slip of one configuration.

FIG. 9 shows the further embodiment in which the pillow slip 30 is a generally rectangular pillow slip 30 rather than one which has the same shape as the pillow shown in FIGS. 1 to 8. The pillow slip 30 of FIG. 9 is of generally loose fit so as to slightly match the contour of the pillow and not interfere with the breathing slots 13 and 14. Whilst the generally rectangular pillow slip 30 shown in FIG. 9 is a possibility it is preferred that the pillow slip have the same general configuration as the pillow as shown by the pillow slip 30 in FIG. 8.

In the preferred embodiment of the invention described with reference to FIGS. 1 to 6 the general contour of the curved surfaces of the limbs 10b, 11a and 10c, 11b as well as the neck support region 11, bridge 12 and head support regions 10 are provided by the upper body portion 72. The upper body portion 72 is preferably formed from resilient sponge-like rubbery or synthetic polymeric material such as foam plastic, for example polyurethane. With other embodiments the final shaping of the pillow to provide the curved surface as previously described can be provided not by shaping the actual body 72 but rather by providing inserts of foam plastics material or soft fill material into the outer cover 72 to provide the final shaping previously described.

The base layer 70 may also be completely free of the upper layer 72 or alternatively releasable ties could be provided on the base layer 70 or upper layer 72 for tying the base layer 70 to the upper layer 72 to merely secure and hold the base layer 70 in position relative to the upper layer 72.

FIGS. 10 to 17 show how the pillow is used and supports a user's head during normal head movement while the person is asleep.

Figure 10:
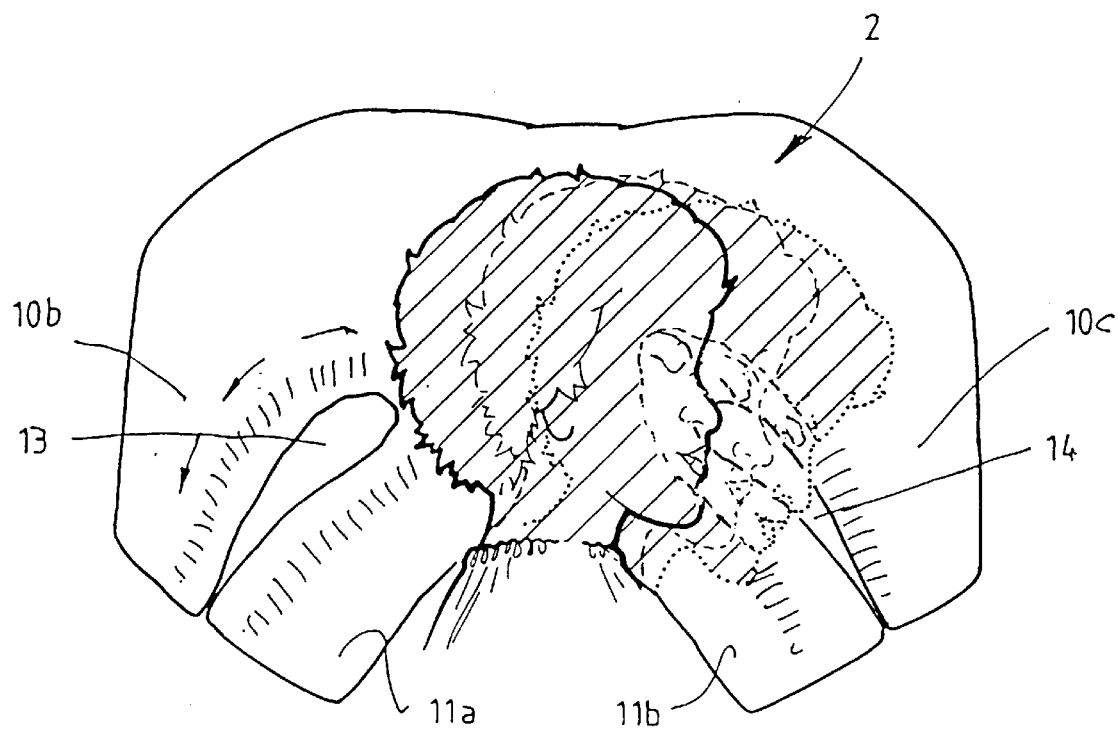
FIG. 10 is a view of a person sleeping on the pillow according to the preferred embodiment of the invention.
Figure 11:
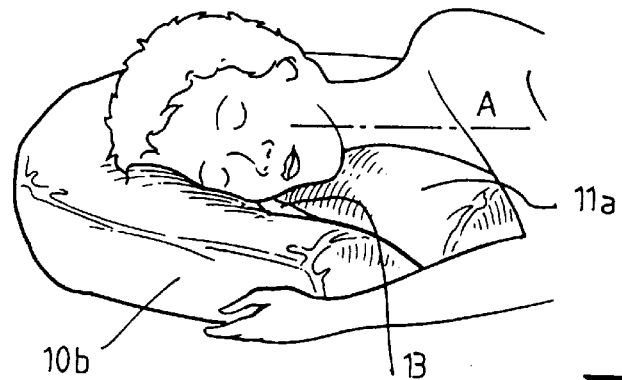
FIGS. 11, 12, 13, 14, 15, 16 and 17 show diagrammatically the attitudes of a person's head when lying asleep in various positions on the pillow.
Figure 12:
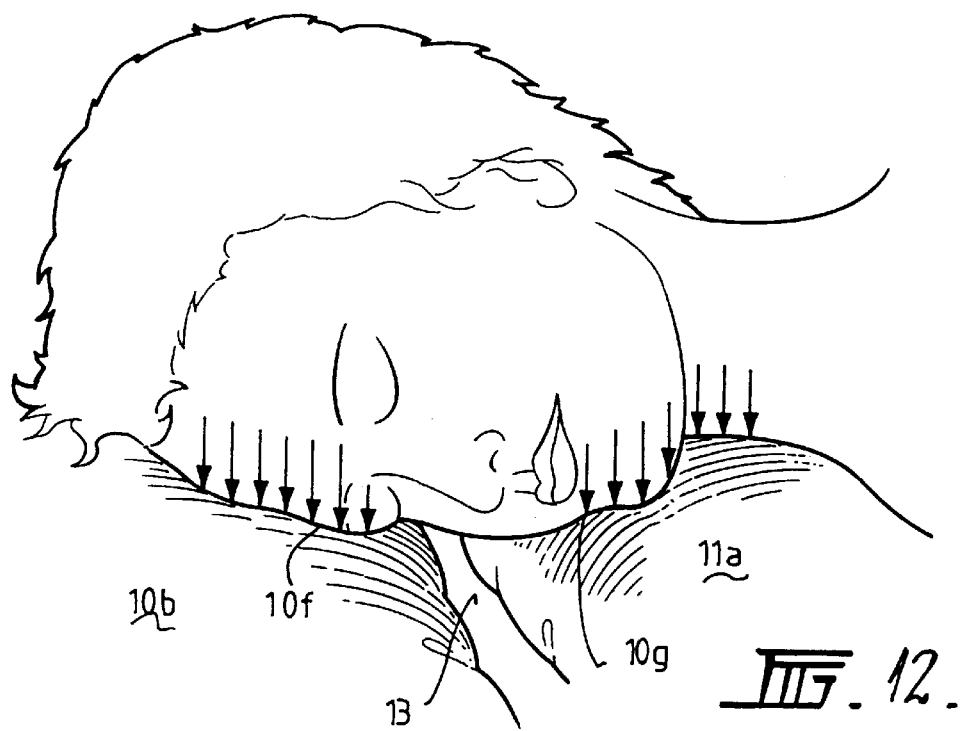
Figure 13:
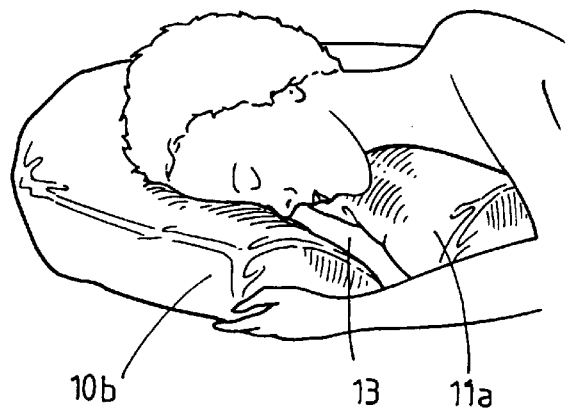
Figure 14:
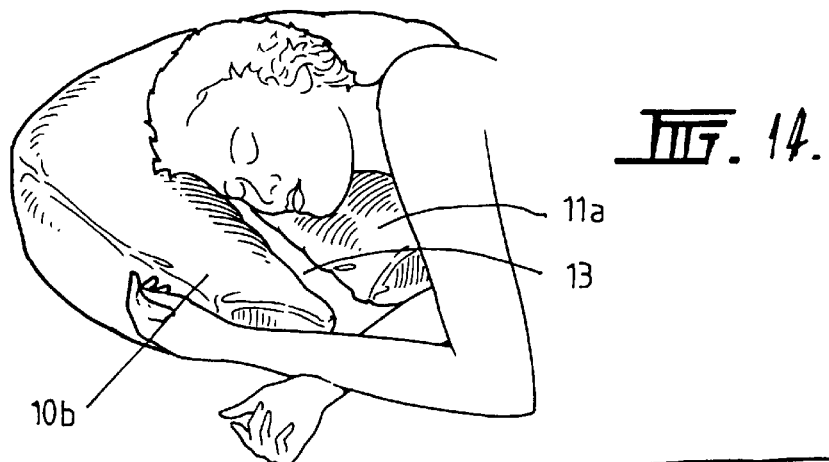
Figure 15:
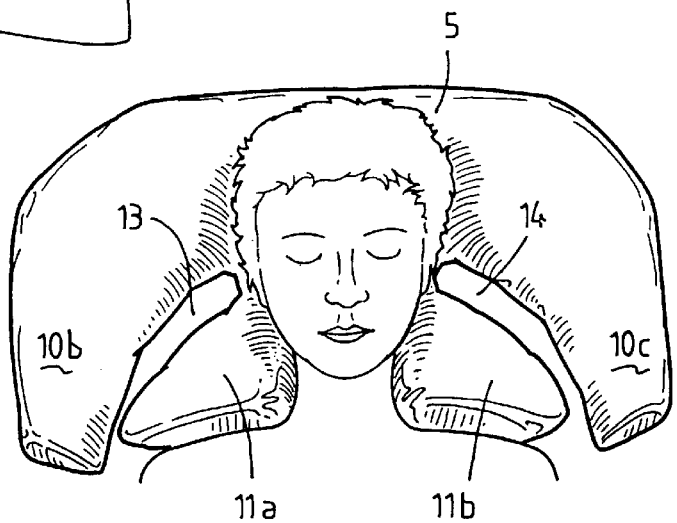
Figure 16:
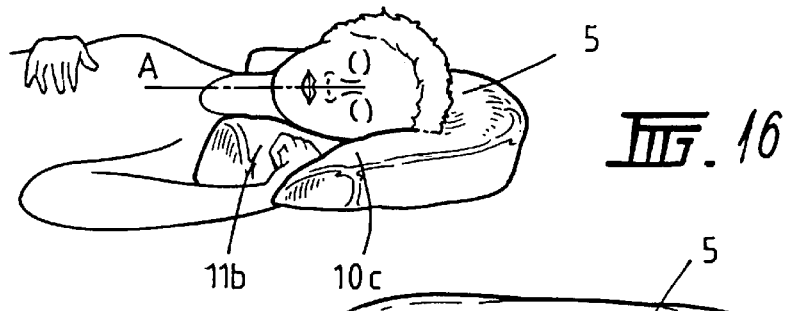
Figure 17:
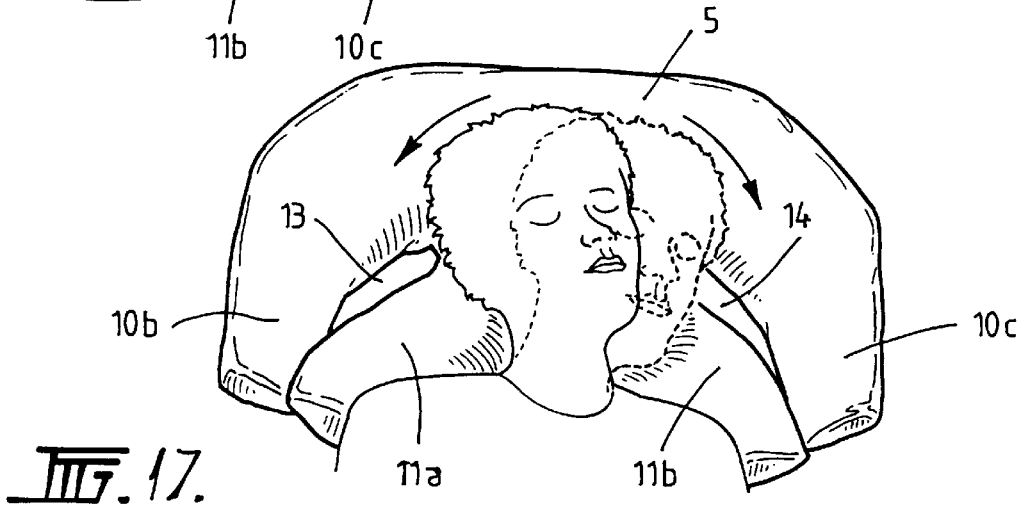

FIG. 10 shows how the head and neck are supported during all natural movements of the neck and head and particularly as the neck naturally relaxes causing the chin to moves towards the chest, and regardless to what degree this happens the weight of the head is distributed evenly by all support sections since the neck and head follow the natural curve of all the support sections—the areas shaded by wide hatch lines show head, neck and chin areas which are supported as the head bends towards the chest. FIG. 11 shows the correct spinal alignment along the line A achieved by the present invention. FIG. 12 shows how sections of the pillow of this invention support a person's head, chin and neck and also shows the gradual reduction of pressure to the face as it enters the open space of the gaps 13, 14—this gradual decrease in pressure gives a great feeling of comfort and leaves no line on the face where the support sections end and the open space begins. FIG. 13 shows a person in prone position and FIG. 14 shows a person sleeping in side or coma position. FIGS. 15 and 16 show a person in supine position with lower limbs of the pillow placed upon a person's shoulders to maintain the head in correctly aligned position as shown in FIG. 16 where the line labelled A denotes spinal axis. FIG. 17 shows a person's head in relation to the pillow when moving the head while sleeping in a supine position.

It should be noted that even when the outer parts of the limbs of the pillow of this invention are in closed up position, nevertheless the top rolled or convex inner surfaces 10f, 10g remain apart so that the breathing air slot or gaps 13, 14 remain open and continuous and therefore unblocked.

It should be particularly noted from FIGS. 10 and 17 that as the head position changes either by falling towards the chest as in FIG. 10 or by moving sideways as in FIG. 17 the nose and mouth region generally remains over the breathing slot or gap between the uppermost points (as identified by reference P FIG. 1C) of the adjacent limbs 10b, 11a or 10c, 11b so that a complete breathing space is always provided and the pillow itself does not contact the mouth or nasal area to block or obstruct the mouth or nasal area. The shape and contour of the slots 13 and 14 also allow easy escape of exhaled air so that a build-up of carbon dioxide is not created in the vicinity of the nose and mouth. This is particularly shown in preferred embodiments where the slots 13 and 14 pass completely through the pillow particularly when the slots 13 and 14 are left open so extremely good ventilation is provided into and out of the slots 13 and 14. Nevertheless, even if the slots 13 and 14 are closed the elongated contour of the slots 13 and 14 and their general size are able to provide more than adequate ventilation to ensure that there is no carbon dioxide build-up.

FIG. 12 shows the pressure being gradually reduced to the user's face in the vicinity of the eyes and mouth by the curved surfaces in 10f and 10g as identified by the arrows in FIG. 12. As can be seen by the arrows pressure is reducing gradually towards the eyes and mouth region and of course no pressure results from the slots of 13 or 14 where no contact is made with the person's face. Thus, the gradual pressure change provides comfortable support and eliminates the possibility of pressure lines or marks on the user's face which may occur if there are abrupt disruptions and change in surface profile of the pillow. In other embodiments not shown the base layer 70 or part of the upper layer 72 may have different degrees of firmness (by being made from different material) in the neck support region 11.

Whilst I have described in the foregoing embodiment one preferred form of my invention it will be understood by those skilled in this art that variations and modifications may be made without departing from the spirit and scope of this invention and I therefore do not wish to be understood as limiting myself to the precise terms used.

What is claimed is:

1. A pillow including:
 a pillow body which has;
 (a) a central portion having a first bed head end and a second foot end;
 (b) a pair of head support limbs extending outwardly from the central portion and curving from the bed head end towards the foot end;
 (c) a pair of neck, chin and jaw support limbs extending outwardly from the central portion at the foot end of the central portion and being spaced inwardly of the head support limbs;
 (d) a breathing space being defined between each adjacent head support limb and neck, jaw and chin support limb, the breathing space extending from an intermediate position of the central portion between the bed head end and the foot end of the central portion outwardly and towards the foot end of the central portion; and
 (e) the head support limbs and neck, jaw and chin support limbs each having an upper top surface, a lower bottom surface and an inner surface joining said upper top surface and lower bottom surface, said inner surfaces being curved downwardly from an upper position on said upper top surfaces of the limbs towards a bottom position adjacent said lower bottom surfaces of the limbs so that the breathing spaces taper from a relatively wide opening between the upper positions of the limbs to a relatively narrower opening at the bottom positions of the limbs.

2. The pillow of claim 1 wherein the pillow body includes a separate base section which can be removed to alter the height of the pillow.

3. The pillow of claim 1 wherein the pillow has a cover conforming in shape to the pillow body.

4. The pillow of claim 3 wherein the cover has an inner liner to form a pouch between the cover and the inner liner for receipt of soft filling material so that soft filling material can be included in the pouch to change the height and/or shape of the pillow, the inner liner extending along at least part of the length of the neck, jaw and chin limbs and the central portion adjacent the foot end of the pillow.

5. The pillow of claim 1, including cuts provided in the central portion extending inwardly from the breathing space for accommodating movement of the limbs with respect to one another and the central portion.

6. The pillow of claim 1 wherein the bed head end of the pillow is provided with a V-shaped profile to assist in movement of the head support limbs with respect to the central portion.

7. The pillow of claim 1 wherein the breathing spaces are in the form of open spaces extending completely through the pillow.

8. The pillow of claim 1 wherein additional soft filling may be provided for location between the pillow body and the outer cover for changing the height and/or contour of the central portion or limbs.

9. The pillow of claim 1 wherein the pillow body and the outer cover are provided in a pillow slip.

10. The pillow of claim 1 wherein the upper surface of the pillow body is convoluted or egg carton shaped.

* * * * *